(12) United States Patent
Eide et al.

(10) Patent No.: US 7,640,109 B2
(45) Date of Patent: Dec. 29, 2009

(54) FINGERPRINTING OF COMPLEX HYDROCARBON CONTAINING MIXTURES

(75) Inventors: Ingvar Eide, Trondheim (NO); Kolbjorn Zahlsen, Trondheim (NO)

(73) Assignee: Statoil ASA, Stavanger (NO)

( * ) Notice: Subject to any disclaimer, the term of this patent is extended or adjusted under 35 U.S.C. 154(b) by 409 days.

(21) Appl. No.: 10/587,805

(22) PCT Filed: Feb. 7, 2005

(86) PCT No.: PCT/GB2005/000412

§ 371 (c)(1),
(2), (4) Date: Dec. 18, 2006

(87) PCT Pub. No.: WO2005/075972

PCT Pub. Date: Aug. 18, 2005

(65) Prior Publication Data

US 2008/0210856 A1    Sep. 4, 2008

(30) Foreign Application Priority Data

Feb. 6, 2004    (GB) ................... 0402639.9

(51) Int. Cl.
*G06F 19/00*    (2006.01)
(52) U.S. Cl. ........................................... 702/2
(58) Field of Classification Search ............... 702/2, 702/6, 9, 22, 23; 436/29, 30, 31
See application file for complete search history.

(56) References Cited

U.S. PATENT DOCUMENTS

| | | | |
|---|---|---|---|
| 5,190,882 A | 3/1993 | Schulz et al. | 436/139 |
| 5,242,602 A | 9/1993 | Richardson et al. | 210/745 |
| 5,600,134 A | 2/1997 | Ashe et al. | 250/252.1 |
| 5,672,869 A | 9/1997 | Windig et al. | 250/282 |
| 5,699,269 A | 12/1997 | Ashe et al. | 702/30 |
| 5,747,806 A | 5/1998 | Khalil et al. | 250/339.12 |
| 5,862,512 A * | 1/1999 | Voorhees et al. | 702/2 |
| 6,096,553 A | 8/2000 | Heald et al. | 436/40 |
| 6,100,975 A | 8/2000 | Smith et al. | 356/301 |
| 6,229,652 B1 | 5/2001 | Bajt et al. | 359/584 |
| 6,275,775 B1 | 8/2001 | Baco et al. | 702/25 |
| 2004/0164237 A1 | 8/2004 | Jones et al. | 250/269.1 |

FOREIGN PATENT DOCUMENTS

| | | |
|---|---|---|
| EP | 0834071 | 4/1998 |
| WO | 2004/102169 | 11/2004 |

* cited by examiner

*Primary Examiner*—Kiet T Nguyen
(74) *Attorney, Agent, or Firm*—McCormick, Paulding & Huber LLP

(57) ABSTRACT

The invention provides a method of analysing a complex hydrocarbon-containing mixture, the method comprising the steps of: obtaining a liquid sample of the complex hydrocarbon-containing mixture; injecting the sample into a liquid carrier flowing to a mass spectrometer, wherein the mass spectrometer is set so as to ionise molecules in the sample without causing fragmentation thereof; recording a mass spectrum for ions obtained from the sample; and using the mass spectrum to obtain fingerprint of the mixture. äIn one embodiment, two or more mass spectra are recorded and are combined to obtain a fingerprint of the mixture.

14 Claims, 7 Drawing Sheets

FINGERPRINTING OF COMPLEX HYDROCARBON CONTAINING MIXTURES

CROSS-REFERENCE TO RELATED APPLICATIONS

This application claims the benefit of PCT Application No. PCT/GB2005/000412, filed on Feb. 7, 2005, which claims the benefit of Great Britain Patent Application No. GB 0402639.9, filed on Feb. 6, 2004, the disclosures of which are hereby incorporated by reference in their entireties.

FIELD OF THE INVENTION

The present invention relates to a method of analyzing samples of complex hydrocarbon-containing products and has particular relevance, amongst other things, to the analysis of samples from oil wells or their vicinity.

BACKGROUND OF THE INVENTION

In hydrocarbon exploration and production there is a need to determine the approximate composition of oil samples in order to determine the origin and properties of the oil. The analysis of oil samples to determine the approximate composition thereof and more particularly, to obtain a pattern that reflects the composition of a sample and that can be recognised, is known in the art as fingerprinting.

There are many known methods of fingerprinting. Most of these methods use gas chromatography (GC) to separate out individual components of a complex hydrocarbon mixture. Some methods use the combination of gas chromatography and mass spectroscopy (GC-MS) to detect spectra characteristic of individual components of the complex hydrocarbon mixture.

Most fingerprinting techniques known in the art are based on the identification and quantification of a limited number of selected compounds which act as marker molecules. One such method is described in U.S. Pat. No. 5,602,755A to Ashe et al. This document discloses a method for predicting the properties of a complex hydrocarbon mixture which comprises selecting one or more known chemical, perceptual, physical or performance properties of the complex mixture and creating a training set from reference samples which contain characteristic molecular species present in the mixture. The training set is produced by GC-MS analysis of the reference samples and is then used to determine a predicted value of the property of an unknown mixture from a GC-MS analysis thereof.

There is a need in the art however for more complete characterisation of very complex hydrocarbon containing mixtures. A method of more complete characterisation has been developed and successfully used on extracts of diesel exhaust particles. This method uses full scan GC-MS analysis of the sample followed by curve resolution of the results of the analysis to obtain peaks and spectra representing individual compounds in the sample. This method is described in Eide et al. 2001. Environ. Sci. Technol. 35, 2314-2318. A problem with this method is that the heavier parts of oils (those with a boiling point of 400° C. to 450° C.) are difficult to analyse. In addition, the use of curve resolution becomes very complicated with crude oils, which are extremely complex mixtures. Still further, the use of GC-MS analysis is time consuming.

An alternative known method uses high resolution GC-MS analysis to give a much higher resolution of spectra obtained than standard GC-MS (about 10 times as many peaks are obtained using the high resolution method). However, in high resolution GC-MS analysis of a number of oil samples, a very long time is needed to carry out each analysis. Using this method, the data obtained may be too complex to allow chromatograms obtained to be resolved into individual peaks and thus interpret the pattern obtained. Further, the method does not work on large (heavy) molecules.

SUMMARY OF THE INVENTION

From a first aspect, the present invention provides a method of analysing a complex hydrocarbon-containing mixture, the method comprising the steps of: obtaining a liquid sample of the complex hydrocarbon-containing mixture; injecting the sample into a liquid carrier flowing to a mass spectrometer, wherein the mass spectrometer is set so as to ionise molecules in the sample without causing fragmentation thereof; recording a first mass spectrum for ions obtained from a first portion of the sample; recording one or more further mass spectra for ions obtained from further portions of the sample; and combining the first and further mass spectra to obtain a fingerprint of the mixture.

Using the method of the invention, a fingerprint of the mixture is obtained by combining at least two mass spectra obtained from a sample of the mixture. By combining two or more mass spectra, the signal to noise ratio in the fingerprint obtained is reduced. Thus, more accurate results are achieved.

Any desired number of spectra of two or more could be used in the method of the invention. Preferably, between 2 and 20 mass spectra will be recorded. More preferably, between 5 and 15 mass spectra are recorded and still more preferably, between 8 and 12 mass spectra are recorded. In a most preferred embodiment, 10 mass spectra are obtained for the mixture and this has been shown to produce accurate, repeatable results.

In one embodiment, only a single mass spectrum could be recorded for the sample. From a further aspect therefore, the present invention provides a method of analysing a complex hydrocarbon-containing mixture, the method comprising the steps of: obtaining a liquid sample of the complex hydrocarbon-containing mixture; injecting the sample into a liquid carrier flowing to a mass spectrometer, wherein the mass spectrometer is set so as to ionise molecules in the sample without causing fragmentation thereof; recording a mass spectrum for ions obtained from the sample; and using the mass spectrum to obtain a fingerprint of the mixture.

A further advantage of the method of the invention is the relatively short time required to produce a fingerprint of a mixture. The time taken to obtain a fingerprint using the method of the invention could be as little as about 30 seconds.

Although the method of the invention is defined above as a method of analysing a complex hydrocarbon-containing mixture, it will be appreciated that the method could also be used to analyse a mixture containing hydrocarbons and/or other organic compounds, e.g. aromatic compounds, mono- or polycyclic compounds, halogenated compounds, surfactants, etc., in particular environmental pollutants such as those deriving from domestic or industrial effluent, leaching of agrochemicals, etc. Thus, the invention extends to the analysis of complex mixtures containing hydrocarbons and/or other organic compounds. For example, the method could be used to analyse a mixture of water and surfactants. Such a modified form of the method of the invention may be defined analogously to the aspects of the invention set out in the appended claims.

In one preferred embodiment of the invention, the method is carried out using a liquid chromatography mass spectrometer from which the liquid chromatography column has been removed. To supply a sample to the mass spectrometer, the sample of the complex hydrocarbon-containing mixture is preferably injected into a continuous flow of eluent fluid to form a plug of the sample within the flow of eluent fluid, and the eluent fluid containing the sample is then supplied to the mass spectrometer for analysis of the sample.

The provision of the sample as a plug or bolus within a flowing eluent fluid helps to ensure rapid data acquisition and analysis of the sample.

In one preferred embodiment of the invention, the full width half maximum of the concentration of the sample in the eluent over time is determined, and each of the first and further mass spectra of the sample are recorded by mass spectral analysis of ions generated during this full width half maximum range of the sample.

Still more preferably, where only one mass spectrum or a small number of spectra are recorded, these are preferably obtained at or close to the maximum concentration range of the sample.

The voltage difference used in the mass spectral analysis of the sample is set so that the sample molecules become charged but do not fragment. This provides characteristic repeatable results from the mass spectral analysis of the sample. The setting required to achieve this is conventional.

Each of the mass spectral analyses of the sample could be carried out using a single ionisation technique. In one preferred embodiment however, the complex hydrocarbon-containing mixture could be ionized by two or more different ionisation techniques and mass spectra could be recorded for the ions obtained by each of the different ionization techniques. The different ionization techniques used will each give a different spectrum, repeatably characteristic of the sample. Thus, by combining the spectra obtained from analyses using two or more different ionisation techniques, a more finely-tuned fingerprint of the mixture may be obtained.

Preferably the different ionisation techniques comprise two or more of the following: positive atmospheric pressure electrospray ionisation; negative atmospheric pressure electrospray ionisation; positive atmospheric pressure chemical ionisation; negative atmospheric pressure chemical ionisation; positive atmospheric pressure photoionisation; and negative atmospheric pressure photoionisation.

In one particularly preferred embodiment, each of the six different ionisation techniques listed above is used in the analysis of the mixture. This will provide particularly accurate results from the analysis of the mixture.

The mass spectra obtained from the analysis of the mixture could be combined in various ways to obtain the fingerprint. In one preferred embodiment the mass spectra obtained are analysed using multivariate data analysis.

The multivariate analysis used could be principal component analysis or alternatively, it could be Projections to Latent Structures.

In one particularly preferred embodiment, the mass spectra obtained for the sample are converted to numerical values; the numerical values are analysed by principal component analysis; and the principal components obtained from the analysis of each mass spectrum are plotted to provide a graphical indication of the nature of the sample. This is particularly advantageous as the differences between various samples are clearly shown by the plots obtained.

In one preferred embodiment, classification and discrimination can be performed in addition to principal component analysis of the numerical values in order to further improve the results obtained.

The fingerprints obtained using the method of the invention can be used to determine the provenance of a mixture such as for example an oil or petroleum-containing mixture. Thus, the invention provides a process for the characterisation of a first complex hydrocarbon-containing mixture, said process comprising: obtaining a fingerprint of said mixture using the method of the invention; comparing said fingerprint with the fingerprints obtained using the method of the invention of other complex hydrocarbon-containing mixtures of known provenance or properties and thereby determining a prediction of the provenance or properties of said first mixture.

The analysis of the first mixture and the other mixtures will desirably be performed in the same apparatus and under the same operating conditions. However different apparatus can be used if the fingerprints are appropriately calibrated, e.g. by running one or more of the mixtures and adjusting the resultant fingerprint to match its known fingerprint—the same adjustment may then be applied to the fingerprint obtained for the "first" mixture before it is compared with the known fingerprints.

The comparison carried out in the process of the invention may show the first mixture to correspond to one or a mixture (in a certain volume or weight ratio) of two or more of the known mixtures, e.g. to show that an oil stream corresponds to a mixture of oil streams from two or more producer wells in a particular weight or volume ratio. Equally the comparison may be used to predict the properties of the first mixture (e.g. physical, chemical or environmental properties etc.). Based on these predictions, appropriate actions can be taken, e.g. addition of additives, dilution with oil from further producer wells, treatment to remove certain contaminants, etc.

As discussed above, the fingerprint of a sample can be obtained in a relatively short time using the method of the invention. Because of this, the method is particularly applicable to control processes of various types. Thus, from a further aspect the invention provides a process for monitoring the progress of a reaction comprising the steps of: taking a sample of the reaction mixture during a reaction; injecting the sample into a liquid carrier flowing to a mass spectrometer, wherein the mass spectrometer is set so as to ionise molecules in the sample without causing fragmentation thereof; recording a first mass spectrum for ions obtained from a first portion of the sample; recording one or more further mass spectra for ions obtained from further portions of the sample; combining the first and further mass spectra to obtain a fingerprint of the mixture; and comparing a plot of the principal components obtained from the analysis of the sample with a plot of the principal components obtained from a sample taken at an earlier stage in the reaction, or with a plot of the principal components for a desired end point of the reaction, to determine the stage reached by the reaction. In this way, the progress of a reaction can be monitored in order to close it down at the appropriate time.

In an alternative aspect, the invention provides a process for controlling a reaction comprising the steps of: taking a sample of a reaction mixture during a reaction; injecting the sample into a liquid carrier flowing to a mass spectrometer, wherein the mass spectrometer is set so as to ionise molecules in the sample without causing fragmentation thereof; recording a first mass spectrum for ions obtained from a first portion of the sample; recording one or more further mass spectra for ions obtained from further portions of the sample; combining the first and further mass spectra to obtain a fingerprint of the mixture; comparing a plot of the principal components obtained from the analysis of the sample with the desired position of the principal components for a sample obtained at desirably optimal reaction conditions; and adjusting the reaction parameters to bring the principal components obtained from the analysis of the sample back towards the desired position. In this way, a reaction can be monitored in order to maintain the desirably optimal reaction conditions (e.g. the reaction can be maintained at optimum steady state conditions).

Preferably, samples are taken and analysed at regular intervals during the reaction and adjustments are made to the reaction parameters in real time in response to the analysis of each sample in order to provide a continuous feedback control process for a reaction.

The method of the invention also has the advantage that several data matrixes are obtained, which can be handled separately or combined. This has the advantage that the data is easier to analyse as the relative size of the data matrixes is smaller and that the matrixes can be compared to one another to be used as internal controls and/or cross bearings.

Normally, no separation of a mixture would be required prior to carrying out the method of the invention. For extremely complex mixtures however, fractionation of the mixture could be carried out prior to commencing the analysis of the invention. The fractionation could be carried out according to differences in polarity or boiling point.

Likewise, where the mixture is discontinuous, e.g. where it is an oil-in-water emulsion such as produced water, the mixture may be pre-treated (e.g. by centrifugation) to concentrate or dilute the discontinuous phase.

The fingerprint obtained by the method of the invention will typically be a data matrix of relative intensities of mass spectral lines at specific m/z ratios or ratio ranges achieved by the use of specific ionization techniques.

BRIEF DESCRIPTIONS OF THE DRAWINGS

Preferred embodiments of the invention will now be described by way of example only and with reference to the accompanying drawings in which.

DETAILED DESCRIPTION OF THE PREFERRED EMBODIMENTS

A method of fingerprinting an oil sample according to the invention is described below. An Agilent 1100 Series LC/MSD system from Agilent Technologies Inc, Palo Alto, Calif., USA is used to analyse the sample. The liquid chromatography column is removed from the machine prior to use. The oil sample is diluted if necessary and a portion of about 1-2 µl thereof is injected into the mass spectrometer part of the system without previous separation on a chromatographic column to be sure that no loss of compound should occur before the mass spectrometric analysis is carried out. The mass spectrometer is operated in the scan mode in the range of m/z=65 to 3000, in intervals of more than 1000. The mass spectrometer used may be an M+ stepped in 0.1 mu increments and with 1 mu resolution.

It will be appreciated that although the present example is carried out using a single quadrupole type LC-MS machine, and this is particularly effective for the purpose of chemical fingerprinting, any type of LC-MS machine could be used to carry out the method of the invention. Thus for example, other types of LC-MS machines such as ion trap, time of flight and high resolution machines could also be used.

Figure 1:
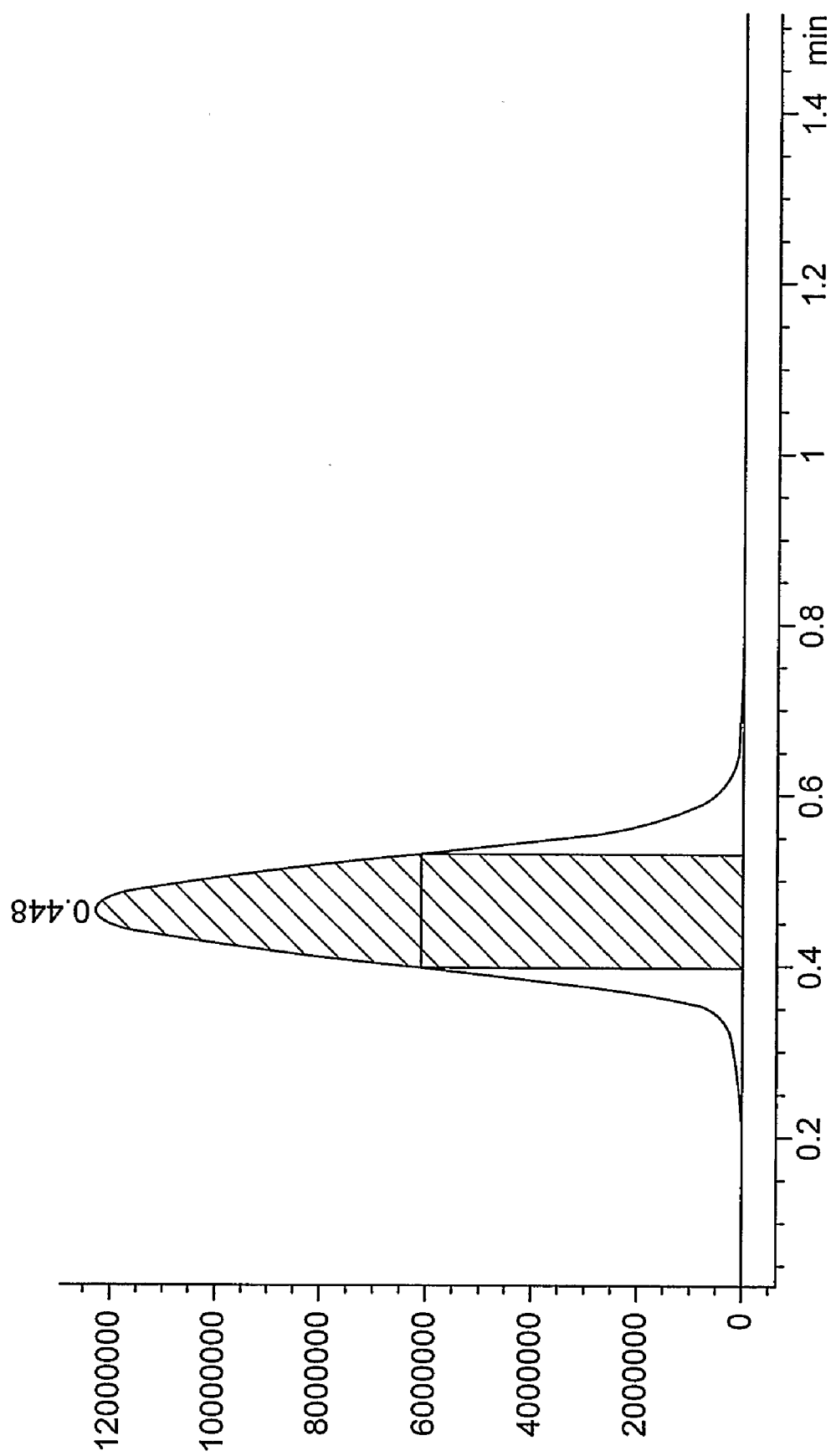
FIG. 1 is a graph showing the concentration against time of a plug of sample.

For injection of the sample to the mass spectrometer, liquid eluent is fed directly to the mass spectrometer to provide a continuous flow. In one preferred embodiment, the eluent consists of acetonitrile and ammonium acetate (50 mM) at a ratio of 90:10. The flow rate of the eluent is 0.2 ml/min. It will be appreciated however, that other eluents could equally well be used. For example depending on the chemicals present in the samples being analysed, any of acetonitrile, ammonium acetate, methanol, or formic acid may be used either alone or in combination. The sample is rapidly injected into the flow of the eluent in order to form a bolus or plug of sample in the liquid eluent, having a width (full width at half maximum) of a number of seconds. FIG. 1 is a graph showing the concentration of the sample within the eluent over time. In one embodiment, the use of autosampler injection allows a high throughput analysis of multiple samples.

MS spectra are extracted from the most intensive part of the signal, i.e. over the full width at half maximum (FWHM) portion of the plug as shown by the shaded portion in FIG. 1. By running analyses over the full FWHM portion of the sample plug, about 10 mass spectra can be collected (the FWHM interval being between about 3 to 10 seconds). By combining each of the spectra obtained (by adding and averaging the spectra), a better resolution and reproducibility is obtained than if only a single analysis is run for a sample. However, less than 10 spectra could be run where a lower number would provide sufficiently accurate results.

The voltage difference at the liquid inlet to the mass spectrometer is set so that the molecules in the sample become charged when injected into the mass spectrometer but do not fragment. Thus for example, the voltage could be set at 100V. Non-fragmentation of the sample molecules is important as this allows a reproducible characteristic MS pattern to be obtained for the sample. In one embodiment of the invention, only a single ionisation technique is used for the repeated MS analysis of the samples.

Using the method described, a satisfactory fingerprint of an oil sample can be obtained within about 30 seconds and this timescale would also be similar for other types of complex hydrocarbon mixtures. This is much quicker than the time taken by known techniques such as gas- and liquid chromatography mass spectrometry (GCMS, LCMS).

In an alternative embodiment of the invention, analysis is carried out on more than one plug of the sample and different ionisation techniques are used in the analysis of the different sample plugs. Two or more different ionization techniques can be used. The six different ionisation techniques which can be used are: positive atmospheric pressure electrospray ionisation; negative atmospheric pressure electrospray ionisation; positive atmospheric pressure chemical ionisation; negative atmospheric pressure chemical ionisation; positive atmospheric pressure photoionisation; and negative atmospheric pressure photoionisation. Each of the six different ionisation techniques will give a different result from the MS analysis of the same sample. Each of these are reproducibly characteristic of the sample. By using more than one ionisation technique and combining the MS results thereof for subsequent analysis, more accurate results can be obtained.

The analysis described above can be carried out on a number of different oil samples. Each MS analysis carried out using a different ionisation technique results in a matrix of data. Each row in each matrix obtained represents the compositional pattern of the identified compounds in that portion. Each column of the matrix represents one compound, or two or more compounds that are very similar as each MS analysis detects integer masses (m/z).

Multivariate data analysis or pattern recognition is used to evaluate similarities between the tested oil samples and for classification and discrimination. Furthermore, regression analysis is used to correlate chemical fingerprints of the samples (the X matrix described below) to measured properties thereof (the Y matrix described below).

Multivariate data analysis is performed using the Simca-P 10.0 software, available from Umetrics, Umeå, Sweden. Principal Component Analysis (PCA) (as described in Jackson, J. E. A User's Guide to Principal Components, John Wiley: New York, 1991) is performed on the X matrix (the chemical fingerprints) for the evaluation of similarities between oil samples. Regression modeling is performed with Projections to Latent Structures, PLS (as described in Wold, S.; Ruhe, A.; Wold, H.; Dunn III, W. J. SIAM J. Sci. Stat. Comput. 1984, 5, 735-743). PLS finds the relationship between the response matrix Y (measured properties) and the matrix X (chemical fingerprints) by simultaneous projections of both the X and Y spaces to a plane or hyperplane (as described in Kvalheim, O. M. Anal. *Chim.* Acta 1989, 223, 53-73, and Kettaneh-Wold, N. *Chemom. Intell. Lab. Syst.* 1992, 14, 57-69). The purpose is to reduce the number of dimensions and obtain the structure in the data. The PLS models are validated with respect to goodness of fit ($R^2$) and goodness of prediction ($Q^2$). The latter is obtained after cross validation (as described in Wold, S. *Technometrics* 1978, 20, 397-405) and is important to avoid overfit. PLS Discriminant Analysis (PLS-DA) is used for classification and discrimination.

When using more than one ionisation technique, each data matrix may be analyzed separately or in combination with other matrixes. Analyzed separately, they may serve as internal controls of each other and cross bearings for more accurate estimate of the contribution of different oils to an oil sample (e.g. in commingled oils).

The fingerprinting method of the invention can be used for a number of applications. Where desired, it can be used together with pattern recognition to determine properties or components of an oil sample based on the known properties or components of other samples.

The method of the invention is particularly relevant to hydrocarbon exploration and production, e.g. the fingerprinting and pattern recognition approach can be applied to the characterization of naturally occurring crude oils, i.e. natural seeps of hydrocarbons on the sea floor or on the land surface; hydrocarbons extracted from rock samples (i.e. drill cuttings or drilled out core samples) during drilling of exploration and production wells, and hydrocarbons sampled during well testing or during the production phase.

An important issue in the exploration for hydrocarbons is to characterize the hydrocarbons in a certain geological setting with respect to their parent source rock(s). Furthermore, it is of great importance to map the route of hydrocarbon migration from the source rock to the reservoir(s) where they accumulate. The fingerprinting method of the invention may be applied for solving these problems by its ability to identify the hydrocarbons present.

In a production scenario, where one well is producing oil from more than one reservoir zone or several wells are producing from several reservoir zones in a commingled production scheme, the method of the invention may be used to estimate the contribution from each of the producing zones; provided that the fingerprints of the oils from each of the reservoir zones are known.

The fingerprints obtained using the method of the invention may be used as natural tracers.

Classification and discrimination of fingerprint data obtained by the method of the invention may also be used for source identification with respect to environmental issues, e.g. the identification of the source to an oil spill. Such methods may require that a stable part (i.e. a part that is not changed due to external factors such as weathering) of the spectrum is identified and used.

Figure 6:
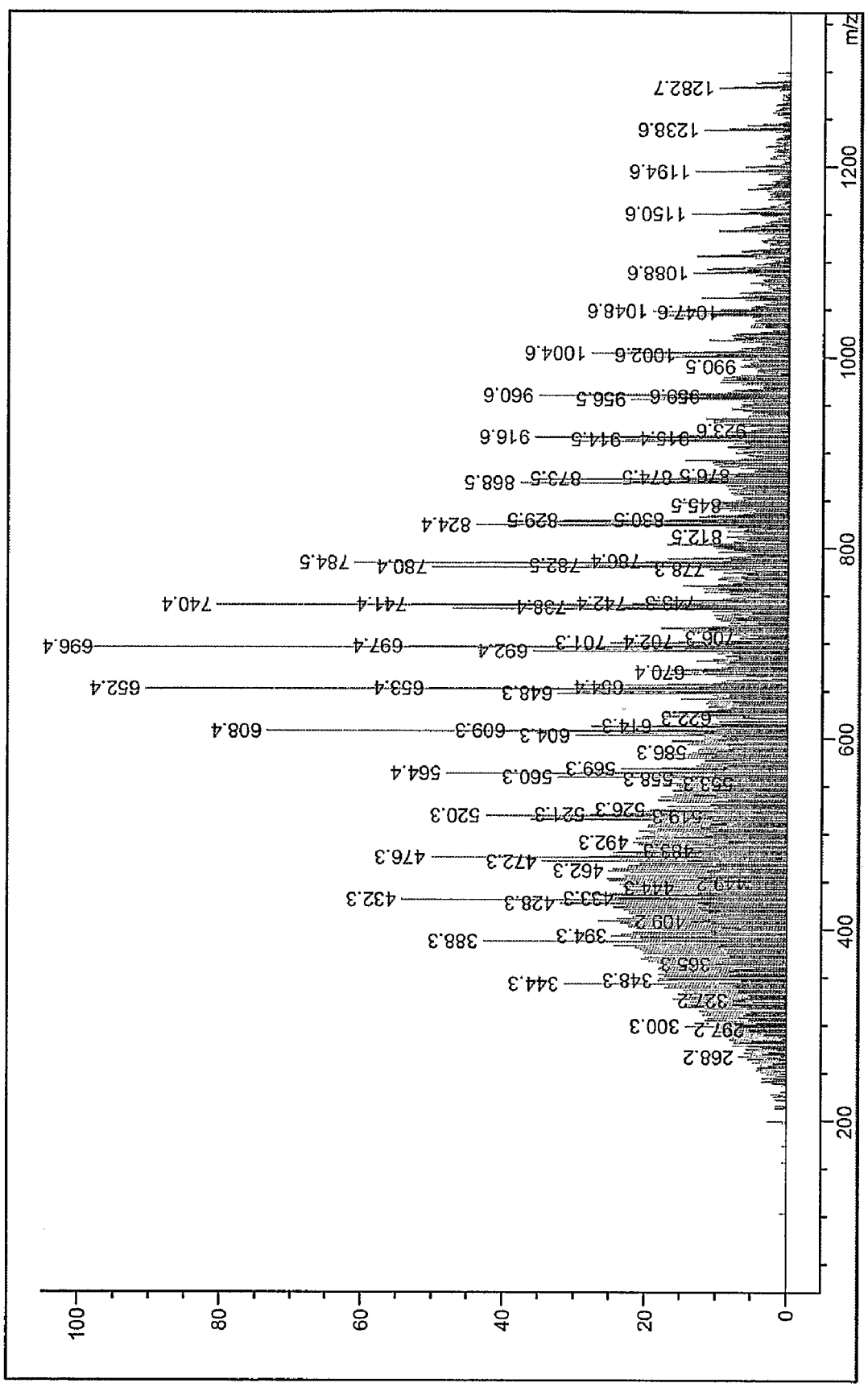
FIG. 6 shows the mass spectra obtained from the analysis of a sample of crude oil containing surfactants.

The method of the invention may also be used for the identification and multivariate calibration of surfactants (for example detergents and emulsifiers) in oil and petroleum products or in water, well treatment chemicals in crude oils or in water, diesel fuel in lubricant oil, biodiesel in regular autodiesel, and so on. A spectrum showing the appearance of surfactants in a crude oil is shown in FIG. 6.

Generally, the fingerprinting method of the invention may be used for the characterization of crude or refined oils and other mixtures of hydrocarbons and other organics. The method may also be used for heavy crude oils. The method can also be used to correlate spectra obtained to a blend matrix, i.e. to determine the contribution to the spectra made by each oil in a mixture. This is known as multivariate calibration.

The method of the invention may also be used for time studies of changes in composition of crude and refined oils, e.g. due to ageing, degradation, upgrading, etc.

Classification and discrimination of fingerprint data obtained by the method of the invention may be used for the identification of compounds that make samples different, e.g. to identify contaminants in crude or refined oils. This has not previously been possible due to the difficulty in identifying a single compound in a very complex mixture. Further, the method of the invention could be used to identify one or more mass lines in the spectra obtained which were of particular relevance. These could then be subjected to further analysis.

The chemical fingerprints obtained by the method of the invention may also be correlated to measured chemical, physical or environmental properties of oils using the Multivariate data analysis and regression modeling techniques described above. The regression models may subsequently be used for the purposes of predicting chemical, physical or environmental properties of other oils.

Figure 2:
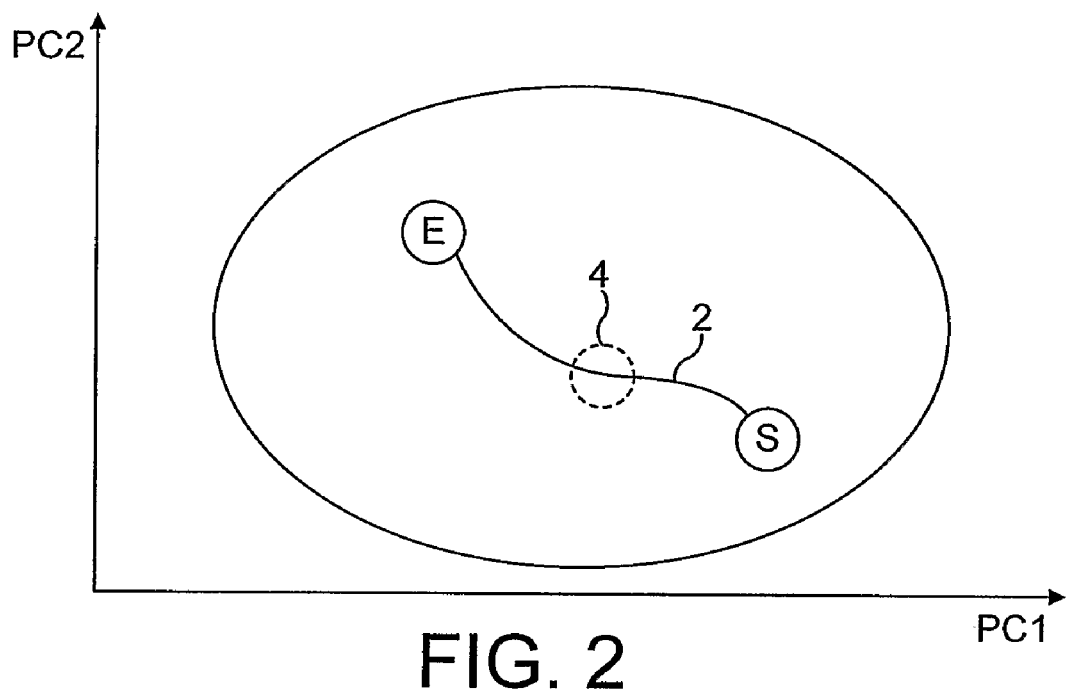
FIG. 2 is a plot of the first two principal components obtained from principal component analysis of each of a number of samples taken at different stages during a reaction.

In addition to the above, as a sample can be analysed relatively quickly and data from the analysis can also be readily obtained, the method of the invention can be used to monitor chemical processes using complex mixtures in real time. In one embodiment, the scores obtained from Principal Component Analysis of the data matrix obtained from the mass spectral analysis of a sample taken during a reaction can be plotted in order to monitor the progress of a reaction such as a fermentation reaction. FIG. 2 is a diagram showing how a score plot might vary over time during a reaction. As shown in FIG. 2, the first principal component (PC1) for each mass spectrum is plotted against the second principal component (PC2) for that mass spectrum, the principal components resulting from the principal component analysis of each spectra obtained.

In the embodiment of FIG. 2, a sample is analysed at the start of a reaction and each of the points obtained from the Principal Component Analysis of the spectra obtained from that sample fall within an area S. The points at the desired process endpoint are known to fall within a second different area of the PC plot, area E. The locus of the plot during the reaction, shown by the line 2 extending between S and E, is also known. Thus, the reaction can be monitored to check that it is on track by plotting data obtained from a sample taken at a known time during the reaction and verifying that the plot falls approximately on the line 2 as shown by the area 4 shown in dotted lines. Using this method, the process can also be stopped at the desired endpoint.

Figure 3:
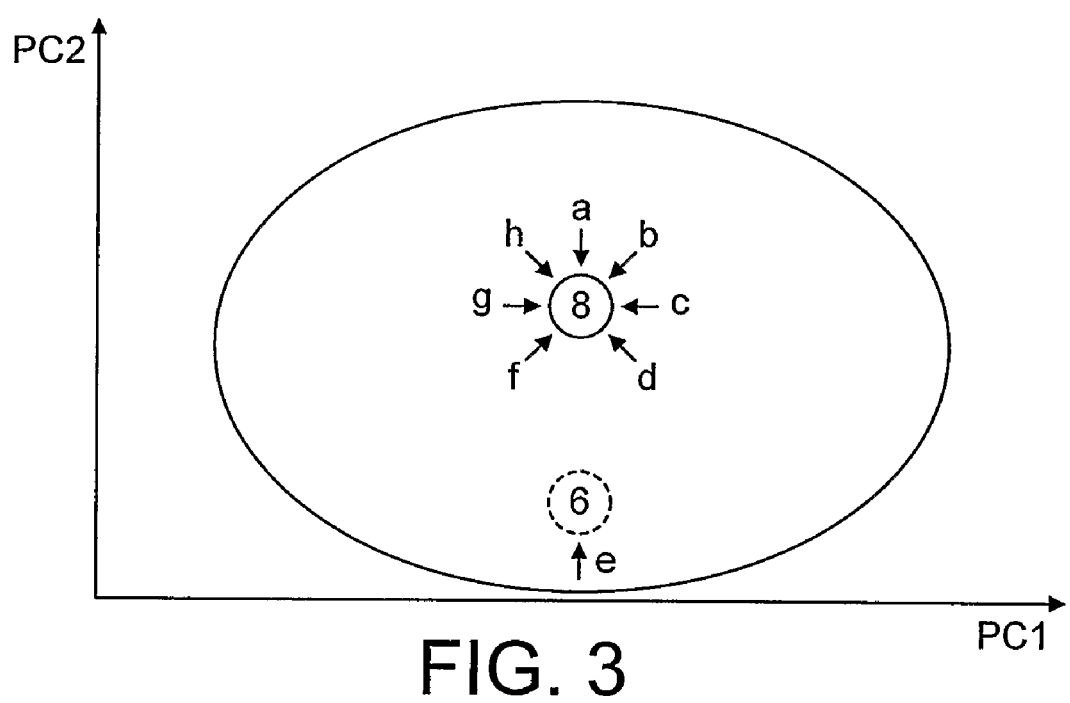
FIG. 3 is a plot of the first two principal components obtained from principal component analysis of a sample taken during a reaction, showing the adjustments necessary to bring a reaction back to optimum steady state conditions.

In an alternative embodiment, the Principal Component plots obtained for a sample taken at a known time during a reaction could be used to provide feedback control to modify process parameters to keep the steady state of the reaction at optimal or desired conditions. This is shown schematically in FIG. 3 which shows how the Principal Component score plot 6 obtained for a sample taken from the reaction at a given time may differ from the known optimal plot 8. Each of the arrows a to h denote a parameter change required to move the score in the direction of the arrow. In the example shown in FIG. 3, the parameter change e would be made in order to bring the score back to the optimal region 8. The process feedback control could be implemented continuously (or at desired intervals) throughout a reaction.

The methods of monitoring a reaction described herein are particularly relevant to biological reactions. One particular reaction to which the methods could be applied is the large scale bacterial fermentation reaction described in International patent application No. WO03/016460 in the name of Norferm DA.

An example of an analysis of three different samples of crude oil is given below. Samples of three different crude oils (CR 1, CR 2, and CR 3) were dissolved in dichloromethane (2 mg/ml), and were analysed by full scan mass spectrometry on an Agilent 1100 Series LC/MSD system (Agilent Technologies Inc., Palo Alto, Calif., USA). Portions of 1 µi were injected into the mass spectrometer without separation on a chromatographic column. Each of the three samples were injected into the mass spectrometer and then analysed ten times to obtain ten separate mass spectra. (A lower number of mass spectra may be sufficient to provide accurate results in some cases however). Each sample takes only about 1 minute to analyse in full. The mass spectrometer was operated in the scan mode in the mass number (m/z) range from 65 to 1000. One ionisation technique was used in the present example: Atmospheric Pressure Electrospray Ionisation (AP-ESI).

Figure 4:
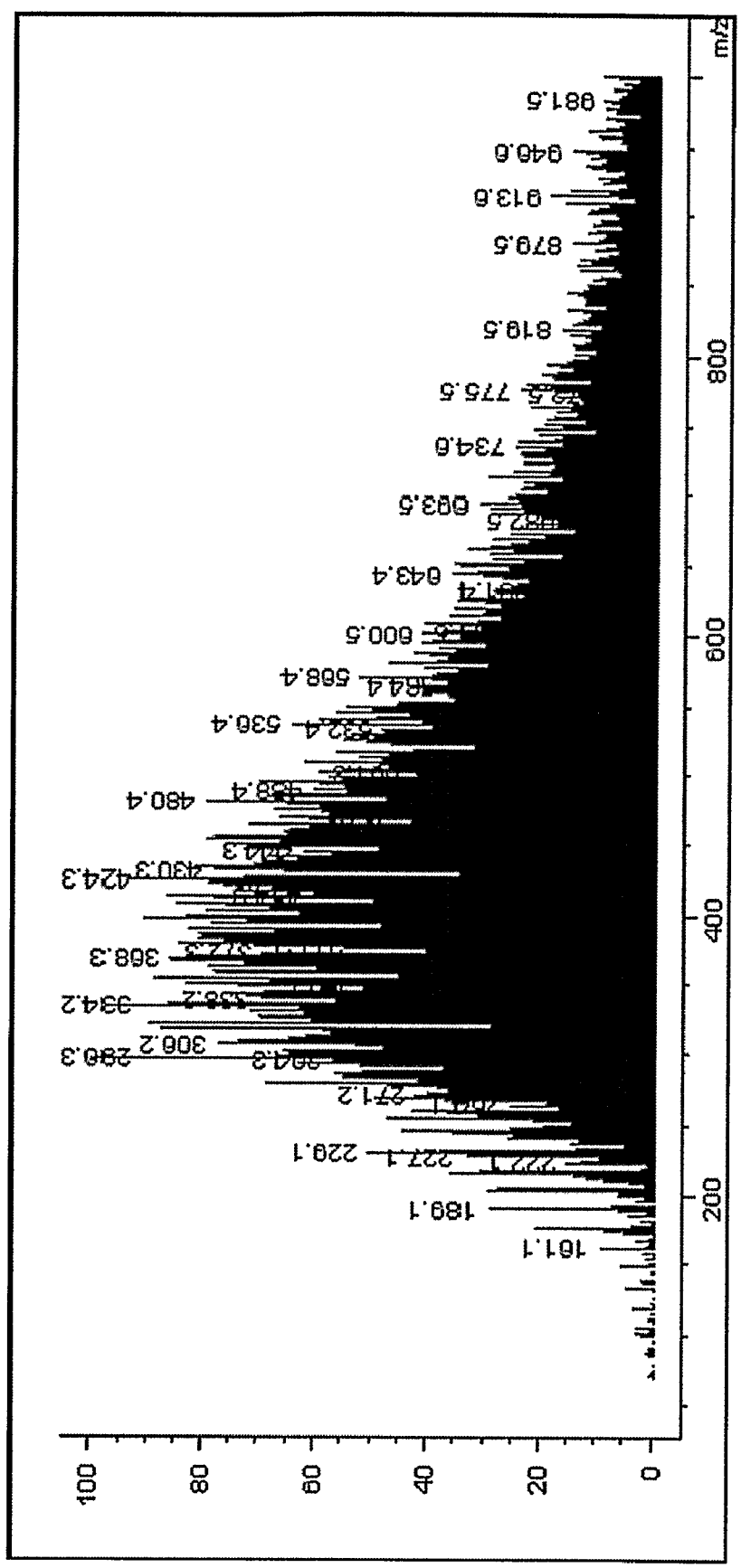
FIG. 4 shows the mass spectra obtained from the analysis of three samples of crude oil.
Figure 4:
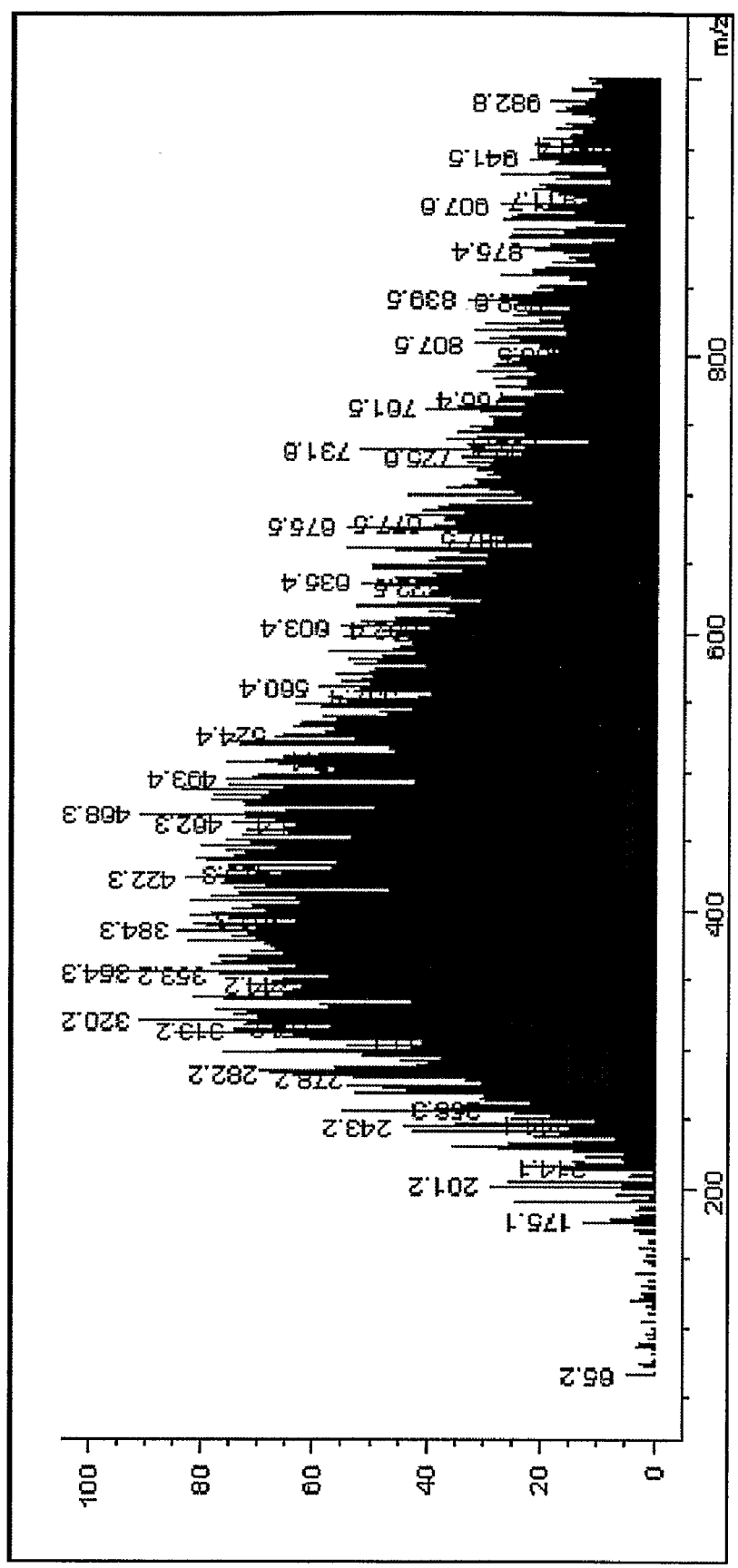
Figure 4:
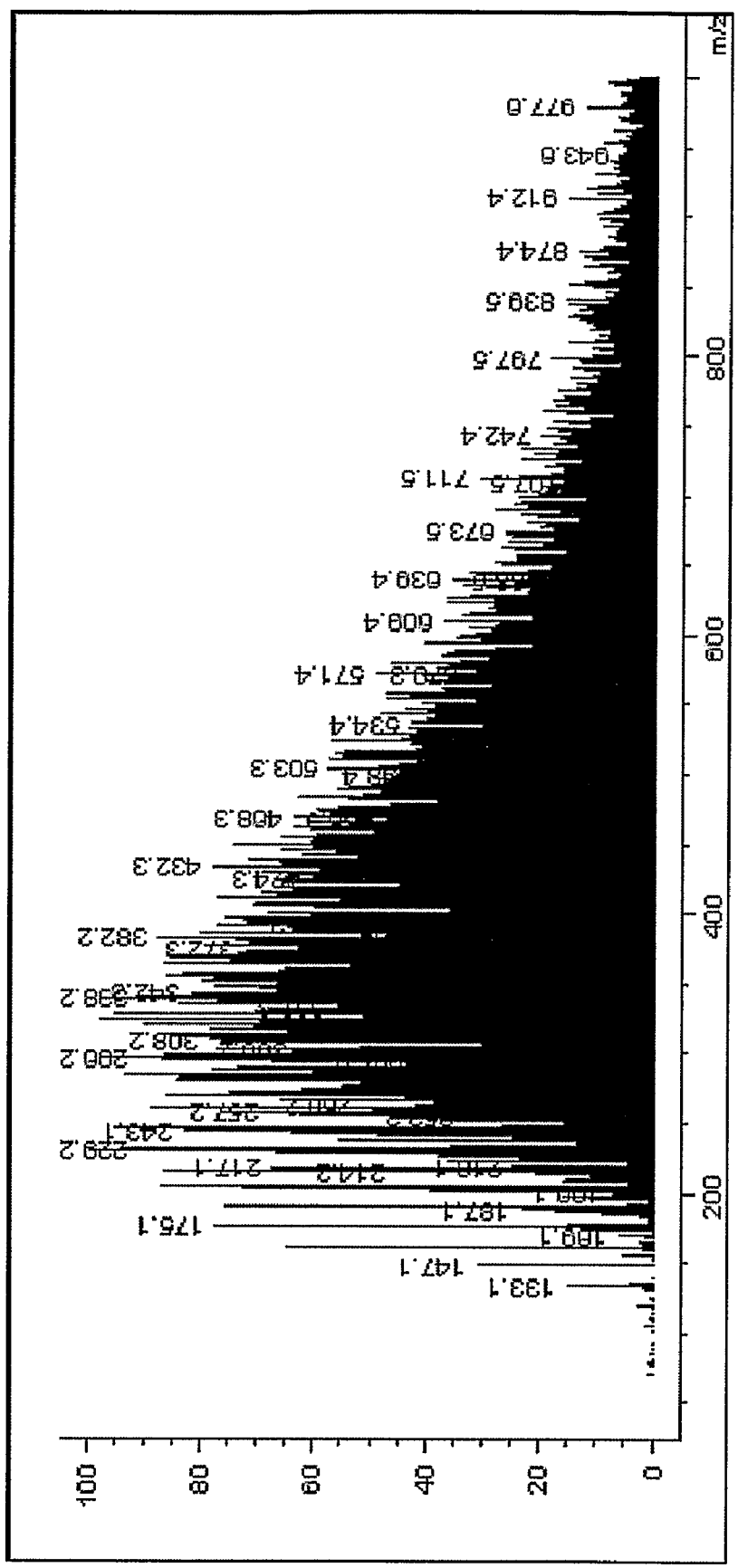

The analysis of the sample is carried out without chromatographic separation (the chromatographic column is removed from the mass spectrometer). However, this does not matter as the purpose is to obtain one spectrum per analysis. The ionisation of the samples is carried out in such a way as to avoid fragmentation. The spectra obtained reflect those molecules in the samples that have been ionised, i.e. they show the compositional pattern of the ionised compounds. FIG. 4 shows one spectrum obtained from each of the three crude oils. There is one distinct spectral line per mass number. The overall profiles of the three spectra appear to be quite similar, although differences between them can be seen. However, the fine, detailed structure in the spectra can be explored systematically by pattern recognition (multivariate data analysis). Each spectrum is therefore converted to a row with numbers, each number represents the height of each spectral line. In the present example, each of the three crude oils were analysed 10 times, and consequently the final data matrix contains 30 rows (one row per analysis) and 935 columns (one per integer mass number).

Figure 5:
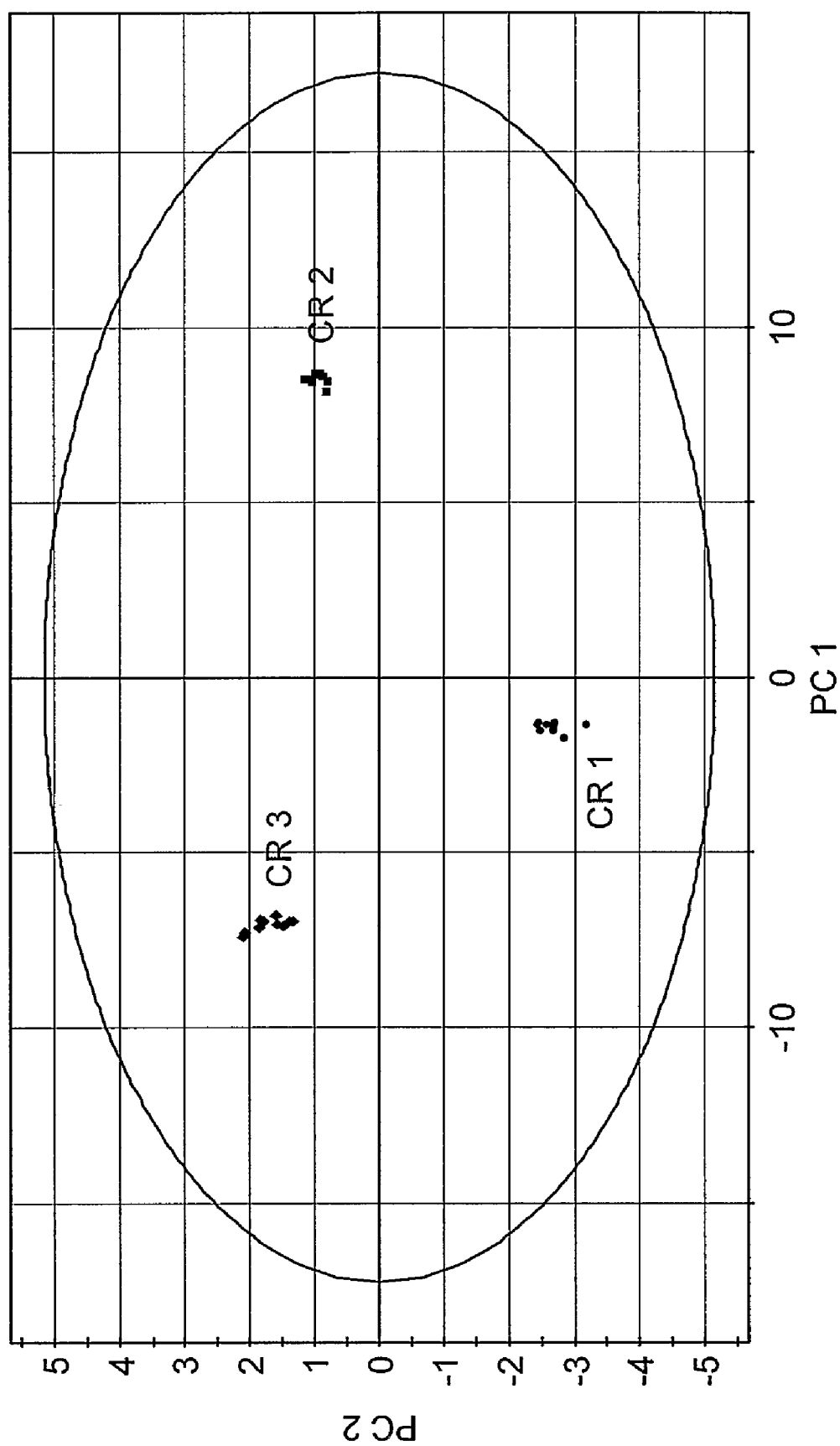
FIG. 5 shows a plot of the scores obtained from principal component analysis of the mass spectra of FIG. 4.

Prior to analysing the data, data pre-processing was performed to improve the accuracy of the results obtained. The m/z values obtained from the mass spectral analysis are given to one decimal place. As a consequence, and in order to construct a compressed matrix from all the individual analyses carried out, the mass numbers obtained were rounded off to integer mass numbers. In addition, the values of the spectral lines obtained (the abundance data) were normalised to a constant sum (within each analysis). Finally, the data were mean centred prior to being analysed. (In this regard, any known alternative to mean centering could alternatively have been used.) Although not used in this example, other data pre-processing procedures could also be used. For example, spectral filtering by standard normal variate transformation could be used. Similarities between patterns were analysed by Principal Component Analysis (PCA) using Simca-P+ 10.0 (Umetrics, Umeå, Sweden). FIG. 5 shows a score plot (a plot of the two first Principal Components obtained for each spectrum) with three separated groups of sample points implying that the three oils are significantly different in composition, and that they can be classified and discriminated from their spectra. The software that was used to analyse the data to produce this score plot was Simca-P+ 10.5 (Umetrics, Umeå, Sweden). Furthermore, the repeatability is satisfactory.

The invention claimed is:

1. A method of analysing a complex hydrocarbon-containing mixture, the method comprising the steps of:
    obtaining a liquid sample of the complex hydrocarbon-containing mixture;
    injecting the sample into a liquid carrier flowing to a mass spectrometer, wherein the mass spectrometer is set so as to ionise molecules in the sample without causing fragmentation thereof;
    recording a first mass spectrum for ions obtained from the sample; and
    using the mass spectrum to obtain a fingerprint of the mixture.

2. A method as claimed in claim 1, wherein the first mass spectrum is recorded for ions obtained from a first portion of the sample, the method further comprising the steps of:
    recording one or more further mass spectra for ions obtained from further portions of the sample; and
    combining the first and further mass spectra to obtain the fingerprint of the mixture.

3. A method as claimed in claim 2, wherein the sample of the complex hydrocarbon-containing mixture is injected into a continuous flow of eluent fluid to form a plug of the sample within the flow of eluent fluid; and
    the eluent fluid containing the sample is then supplied to a mass spectrometer for analysis of the sample.

4. A method as claimed in claim 3, wherein the full width half maximum of the concentration of the sample in the eluent fluid over time is determined; and
    each of the first and the further mass spectra of the sample are recorded by mass spectral analysis of ions generated during the full width half maximum range of the sample.

5. A method as claimed in claim 2, wherein:
    the mass spectra obtained for the sample are converted to numerical values; the numerical values are analysed by principal component analysis; and
    the principal components obtained from the analysis of each mass spectrum are plotted to provide a graphical indication of the nature of the sample.

6. A method as claimed in claim 1, wherein the sample is ionised by two or more different ionisation techniques and mass spectra are recorded for the ions obtained by each of the different ionisation techniques.

7. A method as claimed in claim 6, wherein the different ionisation techniques comprise two or more of the following: positive atmospheric pressure electrospray ionisation; negative atmospheric pressure electrospray ionisation; positive atmospheric pressure chemical ionisation; negative atmospheric pressure chemical ionisation; positive atmospheric pressure photoionisation; and negative atmospheric pressure photoionisation.

8. A method as claimed in claim 1, wherein a plurality of samples are each analyzed by:
- obtaining a liquid sample of the complex hydrocarbon-containing mixture;
- injecting the sample into a liquid carrier flowing to a mass spectrometer, wherein the mass spectrometer is set so as to ionise molecules in the sample without causing fragmentation thereof;
- recording a first mass spectrum for ions obtained from the sample;
- using the mass spectrum to obtain a fingerprint of the mixture; and
- the mass spectra obtained being analysed using multivariate data analysis.

9. A method as claimed in claim 8, wherein the multivariate analysis used is principal component analysis.

10. A method as claimed in claim 8, wherein the multivariate analysis used is Projections to Latent Structures.

11. A process for monitoring the progress of a reaction comprising the steps of:
- taking a sample of the reaction mixture during a reaction;
- injecting the sample into a liquid carrier flowing to a mass spectrometer, wherein the mass spectrometer is set so as to ionise molecules in the sample without causing fragmentation thereof;
- recording a first mass spectrum for ions obtained from a first portion of the sample;
- recording one or more further mass spectra for ions obtained from further portions of the sample;
- converting the mass spectra to numerical values;
- analysing the numerical values by principal component analysis; and
- comparing a plot of the principal components obtained from the analysis of the sample with a plot of the principal components obtained from a sample taken at an earlier stage in the reaction to determine the stage reached by the reaction.

12. A process for controlling a reaction comprising the steps of:
- taking a sample of the reaction mixture during a reaction;
- injecting the sample into a liquid carrier flowing to a mass spectrometer, wherein the mass spectrometer is set so as to ionise molecules in the sample without causing fragmentation thereof;
- recording a first mass spectrum for ions obtained from a first portion of the sample;
- recording one or more further mass spectra for ions obtained from further portions of the sample;
- converting the mass spectra to numerical values;
- analysing the numerical values by principal component analysis;
- comparing a plot of the principal components obtained from the analysis of the sample with the desired position of the principal components for a sample obtained at desirably optimal reaction conditions; and
- adjusting the reaction parameters to bring the principal components obtained from the analysis of the sample back towards the desired position.

13. A process as claimed in claim 12, wherein samples are taken and analysed at regular intervals during the reaction and adjustments are made to the reaction parameters in real time in response to the analysis of each sample in order to provide a continuous feedback control process for a reaction.

14. A process for the characterisation of a first complex hydrocarbon-containing mixture, said process comprising:
- obtaining a liquid sample of the complex hydrocarbon-containing mixture;
- injecting the sample into a liquid carrier flowing to a mass spectrometer, wherein the mass spectrometer is set so as to ionise molecules in the sample without causing fragmentation thereof;
- recording a first mass spectrum for ions obtained from the sample;
- using the mass spectrum to obtain a fingerprint of the mixture; and
- comparing said fingerprint with the fingerprints obtained of other complex hydrocarbon-containing mixtures of known provenance or properties and thereby determining a prediction of the provenance or properties of said first mixture.

* * * * *